United States Patent [19]
Beard

[11] Patent Number: 4,825,876
[45] Date of Patent: May 2, 1989

[54] ENCAPSULATED BLOOD PRESSURE TRANSDUCER

[75] Inventor: Robert W. Beard, Placerville, Calif.

[73] Assignee: Abbott Laboratories, Abbott Park, Ill.

[21] Appl. No.: 159,356

[22] Filed: Feb. 23, 1988

[51] Int. Cl.⁴ .............................................. A61B 5/02
[52] U.S. Cl. .................................... 128/675; 128/748; 73/754; 73/756
[58] Field of Search .................................... 128/672–675, 128/748; 73/708, 715, 720, 740, 753–754, 756

[56] References Cited

U.S. PATENT DOCUMENTS

| | | | |
|---|---|---|---|
| 4,539,998 | 9/1985 | McCord et al. | 128/675 |
| 4,557,269 | 12/1985 | Reynolds et al. | 128/675 |
| 4,576,181 | 3/1986 | Wallace et al. | 128/675 |
| 4,589,287 | 5/1986 | Dickens | 128/675 X |
| 4,610,256 | 9/1986 | Wallace | 128/675 |
| 4,679,567 | 7/1987 | Hanlon et al. | 128/748 X |

Primary Examiner—Edward M. Coven
Assistant Examiner—Angela D. Sykes
Attorney, Agent, or Firm—Christensen, O'Connor, Johnson & Kindness

[57] ABSTRACT

An apparatus and method for providing a blood pressure transducer suitable for use in a catheter line, for monitoring blood pressure. Two embodiments of the blood pressure transducer (20, 120) are disclosed, both of which include connectors (24) suitable for connection to a catheter line. A flow-through passage (22) extends between the two connectors, in fluid communication with a solid-state pressure transducer chip (36), which is mounted on a chip carrier (34) inside a rectangular-shaped plastic housing (30/130, 32). The chip carrier includes a plurality of formed flat leads (38) connected to the pressure transducer chip, and an extending nib (62) having a passage (66) filled with a silicon gel (64), which couples fluid pressure in the flow-through passage to a pressure sensitive diaphragm (106) on the solid-state pressure transducer chip. Electrical signals are transmitted to and from the pressure transducer chip through a multiconductor lead (40) having a plurality of conductors (42), which make electrical contact with the formed flat leads during assembly of the housing. Use of the preassembled chip carrier and of a solid-state pressure transducer chip which includes its own thermal compensation circuit greatly reduces the assembly cost of the blood pressure transducer.

31 Claims, 8 Drawing Sheets

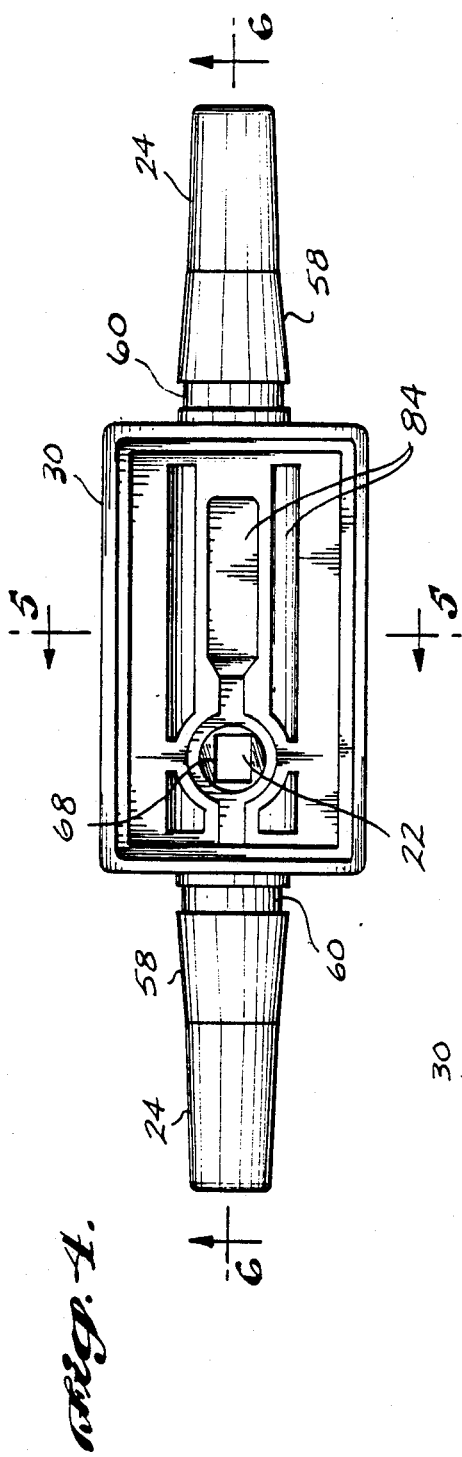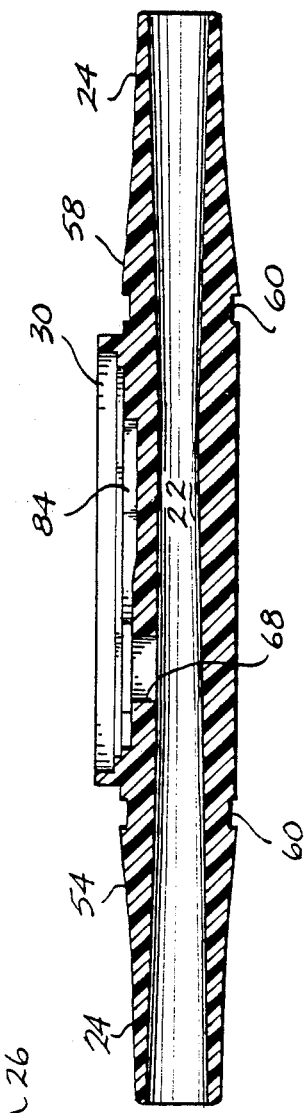

ENCAPSULATED BLOOD PRESSURE TRANSDUCER

TECHNICAL FIELD

The present invention generally pertains to a fluid pressure sensor and, more specifically, to a blood pressure transducer.

BACKGROUND OF THE INVENTION

Knowledge of a patient's blood pressure is often essential to properly assess the patient's medical condition. Continuous monitoring of the blood pressure enables medical personnel to immediately detect changes in the cardiovascular system indicating stress, and to respond rapidly with the appropriate action. Depending on whether a doctor wishes to monitor arterial or venous pressure, a needle may be inserted into an artery or vein, and a very small diameter tube or catheter run through the needle so that its open end is exposed to the fluid pressure of blood at a desired location in the body. If it is necessary to measure blood pressure in an organ, e.g., inside one of the chambers of the heart, the catheter is simply moved through the blood vessel until it is positioned at the desired location. A sterile solution fills the catheter. The pressure of the cardiovascular system at that point in the body is transmitted through the sterile solution to a fluid pressure sensing device connected to the catheter outside the patient's body. The pressure sensing device typically includes a pressure transducer that produces an electrical signal proportional to the fluid pressure of blood at the open end of the catheter. An analog or digital display, or a cathode ray tube connected to the transducer provides an indication of the patient's blood pressure in response to the electrical signal.

In the past, the pressure sensors used to measure and/or monitor blood pressure have been too expensive to routinely discard after a single use. Instead, the pressure sensors have normally been sterilized for reuse on several patients. The time and labor expense involved in preparing conventional blood pressure sensors for reuse is significant. An increased emphasis on stemming the rising cost of medical treatment has created a demand for low cost disposable pressure sensors.

One such disposable blood pressure sensor is described in U.S. Pat. No. 4,576,181. This pressure sensor includes a shell-like housing in which a pressure transducer is directly mounted, covered by an opaque plate that blocks light from reaching a semiconductor surface of the transducer. The opposite surface of the pressure transducer is mounted over a passage in the housing, providing communication with a fluid-filled catheter. A portion of the passage is filled with a gel which serves to hydraulically couple the fluid pressure to the pressure transducer. Mounted within the housing next to the pressure transducer is a dielectric substrate, including a thick film hybrid temperature compensation circuit with pads on which leads entering the housing through an insulated cable are soldered.

Although the disposable blood pressure sensor described above is substantially less expensive than those reusable sensors previously in use, its material and manufacturing labor costs are significantly more than might be desired. Components such as the thick film hybrid circuit provided on the dielectric substrate mounted adjacent the transducer substantially increase its cost. In addition, the labor required to hand assemble the pressure transducer chip within the housing, and to attach the chip to the hybrid circuit and the hybrid circuit to the cable is significant. The hydraulic pressure coupling gel must be injected through one end of the catheter connector into the passage communicating fluid pressure to the transducer. It is difficult to constrain the gel to the desired passage, because it is injected in the form of a low viscosity liquid having a tendency to run.

In consideration of these problems, the present invention seeks to provide an even lower cost disposable blood pressure transducer than that of the above-described prior art. A further object of this invention is to provide a pressure transducer that may be easily assembled with minimal operations requiring hand labor. Yet a further object is to provide an assembly including a premounted pressure transducer that may be readily interfaced to a fluid pathway and electrical leads. These and other objects and advantages of the present invention will be apparent from the attached drawings and the description of the preferred embodiments that follow.

SUMMARY OF THE INVENTION

In accordance with the present invention, an apparatus for measuring pressure in a fluid line includes a solid-state pressure transducer comprising a semiconductor circuit and a pressure sensitive surface. Strain resulting from pressure applied to the pressure sensitive surface while an electrical signal is applied to the pressure transducer through a plurality of contacts disposed on the semiconductor circuit causes the pressure transducer to produce an output signal which varies as a function of the applied pressure.

The apparatus further includes a housing defining a cavity in which the pressure transducer is disposed, and comprising a connector adapted to attach to the fluid line. A fluid passage extends through the housing to a point proximate the pressure sensitive surface of the pressure transducer. Disposed within the cavity is a chip carrier on which is mounted the pressure transducer. The chip carrier includes a fluid interface between the fluid passage and the pressure transducer, and provides means for transmitting fluid pressure between the fluid passage and the pressure sensitive surface.

A plurality of insulated electrical conductors are provided to convey electrical signals to and from the pressure transducer. Associated with the chip carrier is a quick-connect electrical interface between the plurality of electrical conductors and the plurality of connections on the semiconductor circuit of the pressure transducer. The chip carrier further includes means for exposing the pressure sensitive surface to the means for transmitting fluid pressure and isolating an opposite side of that surface from the fluid passage and fluid pressure therein.

Other aspects of this invention are related to a method for assembling a pressure sensing device as defined above, and apparatus for mounting a pressure transducer (i.e., the chip carrier).

BRIEF DESCRIPTION OF THE DRAWINGS

FIG. 4 is a plan view of the lower portion of the housing used in the first embodiment of the blood pressure transducer;

FIG. 5 is a cross-sectional view of the lower portion of the housing taken along section lines 5—5 of FIG. 4;

FIG. 6 is a cross-sectional view of the lower half of the housing, taken along section lines 6—6 of FIG. 4;

DESCRIPTION OF THE PREFERRED EMBODIMENTS

Figure 1:
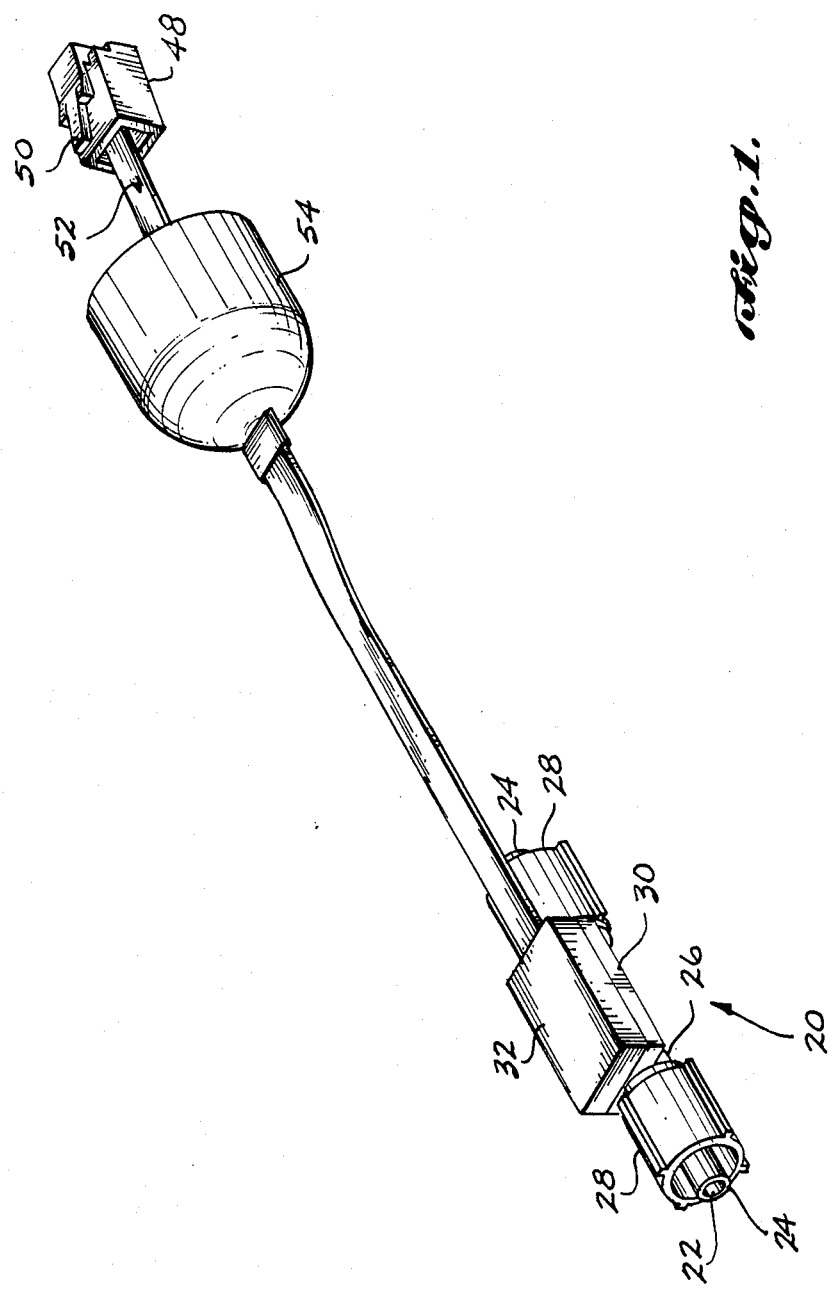
FIG. 1 is an isometric view showing a first embodiment of the blood pressure transducer.
Figure 2:
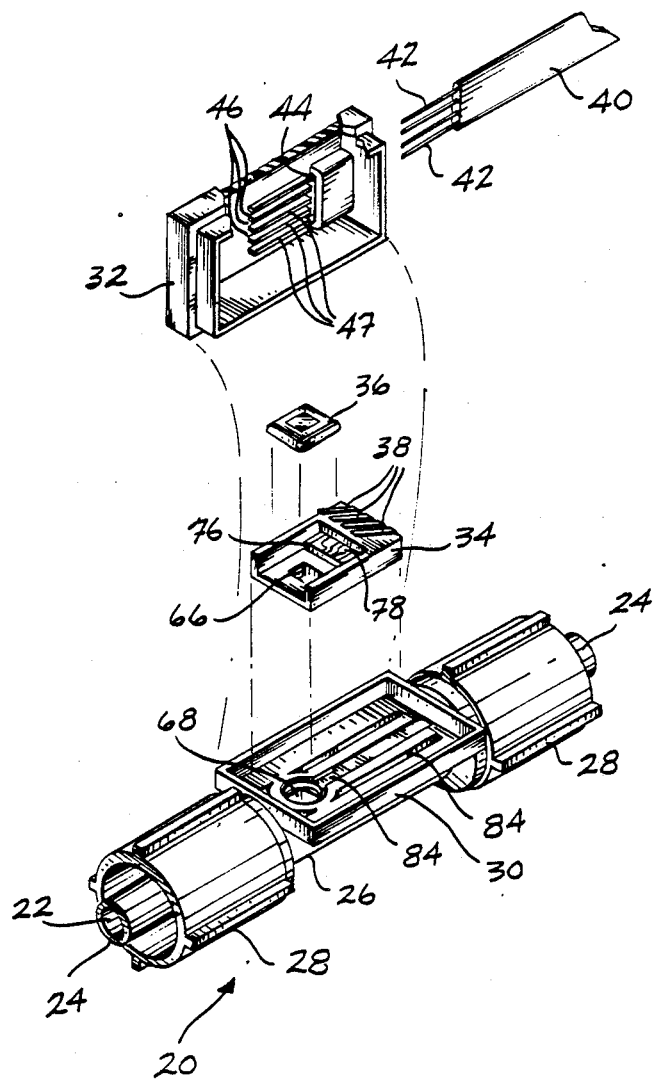
FIG. 2 is an exploded view of the first embodiment, wherein only a portion of the electrical lead terminated in the blood pressure transducer is shown.

A first embodiment of the blood pressure transducer is shown in FIG. 1, generally denoted by reference numeral 20. Blood pressure transducer 20 is intended for use with a catheter, one end of which is inserted into a vein or artery of patient during a medical procedure. The other end of the catheter may be connected to a supply of saline solution or other medical fluid, requiring that the pressure sensor be inserted in the catheter line, i.e., in series connection with the medical fluid supply. To facilitate such use, blood pressure transducer 20 includes a flow-through passage 22, which extends between two catheter connectors 24, disposed at opposite ends of a lower housing portion 30. Internally threaded nuts 28 are provided (seated in grooves 60—see FIG. 3) on each connector to engage the catheter line. The center of flow-through passage 22 is defined by an integral longitudinally extending tubular section 26 on the bottom of lower housing 30. An upper housing section 32 is attached to lower housing section 30 and is connected to a flat multiconductor lead 40. Both upper and lower housing sections are molded of plastic, the upper housing section 32 being opaque to block light transmission.

Multiconductor lead 40 includes four conductors, which carry electrical signals to and from a solid-state pressure transducer chip (not shown in FIG. 1) enclosed within housing sections 30 and 32. The other end of multiconductor lead 40 is terminated in a modular connector 48 of the type commonly used with telephones and includes a press-to-release lever 50, that is adapted to engage a suitable female jack into which connector 48 is inserted. In addition to conductors for conveying electrical signals, lead 40 includes a lumen (not shown), extending between the interior of upper housing 32 and an orifice 52 disposed adjacent modular connector 48. The lumen provides a passage for equalizing the pressure inside upper housing section 32 with ambient air pressure. Lead 40 further includes a rubber shield 54. The shield is normally slid over modular connector 48, protecting it from fluids or other contamination.

Details of the first embodiment of the blood pressure transducer 20 are shown in FIGS. 2 through 8. The internal configuration of the first embodiment, and in particular, the interior of housing sections 30 and 32 is most clearly shown in FIG. 2. With reference thereto, a chip carrier 34 is mounted inside lower housing section 30, positioning a solid-state pressure transducer chip 36 attached thereto in fluid communication with flow-through passage 22. Rather than mounting solid-state pressure transducer chip 36 directly to the interior surface of lower housing 30, the chip is adhesively attached to chip carrier 34 so that a pressure sensitive diaphragm on the lower surface of the chip overlies an orfice 66 formed within the chip carrier. Solid-state pressure transducer chip 36 is electrically connected to a plurality of formed flat leads 38, which extend from a shelf 76. The shelf is molded into chip carrier 34 adjacent the pressure transducer chip. The advantages of the chip carrier and details concerning the solid-state pressure transducer chip and its attachment to the chip carrier are explained below.

Figure 7:
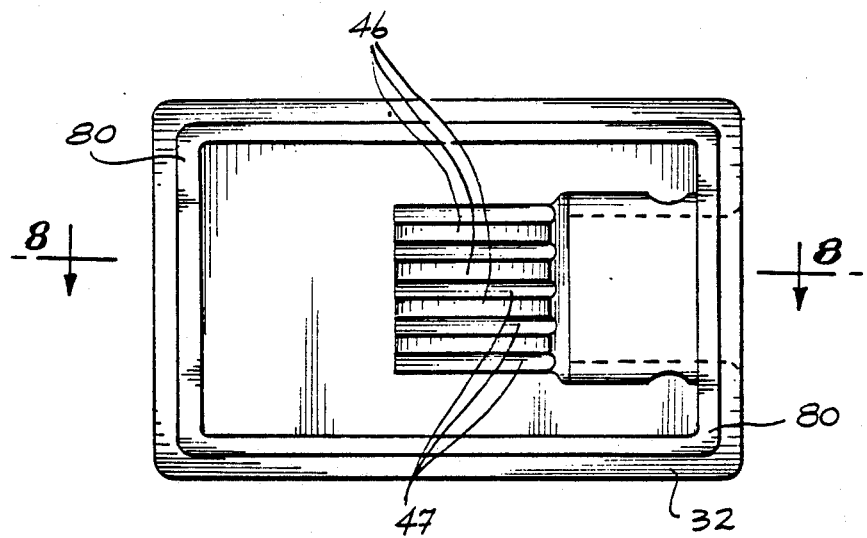
FIG. 7 is a plan view showing the interior of the upper portion of the blood pressure transducer housing.
Figure 8:
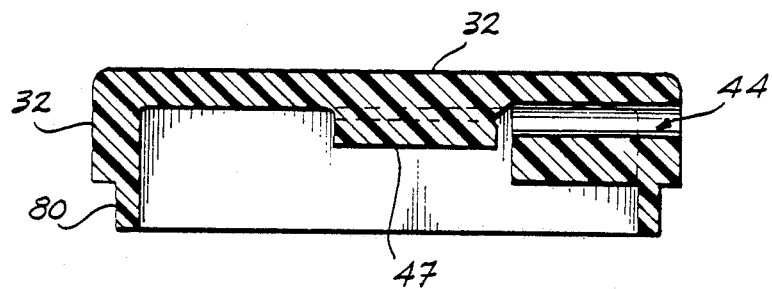
FIG. 8 is a cross-sectional view of the upper portion of the housing, taken along section lines 8—8 of FIG. 7.

The flat leads on the chip carrier are generally formed into a "U-shape," and extend upwardly in parallel alignment with each other above shelf 76. Stripping insulation from the end of lead 40 exposes the ends of the four electrical conductors 42. Since conductors 42 comprise stranded wire, they are twisted and tinned with solder. The exposed conductors are inserted within a slot 44 formed in the upper housing section 32 so that they each lie within separate channels 46, which are defined by parallel aligned ribs 47 on the inner surface of upper housing section 32. Lead 40 is adhesively secured within slot 44. Channels 46 are slightly wider than formed flat leads 38 and are disposed to align with these leads so that the end of each lead is seated within one of the channels 46 upon mating of upper housing section 32 with the lower housing section 30. Details of upper housing section 32 are shown in FIGS. 7 and 8.

Figure 3:
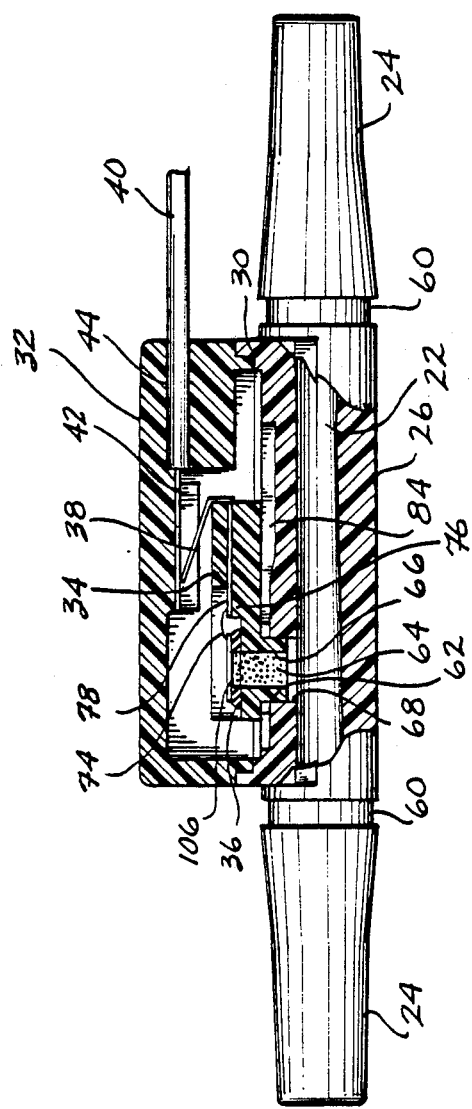
FIG. 3 is a cut-away view showing the first embodiment of the blood pressure transducer in a side elevational view, (wherein the lock nuts on the connectors have been removed for clarity)

With reference to the cut-away view of FIG. 3, the relationship of the chip carrier 34, solid-state pressure transducer chip 36, one of the flat leads 38 and one of the electrical conductors 42 is clearly shown. From this illustration, it is apparent that each of the formed flat leads 38 makes electrical contact with one of the electrical conductors 42 upon assembly of the two housing sections 30 and 32. In fact, the inherent elasticity of formed flat leads 38 causes a continuous spring force to be exerted against the bare ends of conductors 42 by the leads, resulting from the slight displacement of the ends of the flat leads that occurs during the assembly process. This spring force virtually eliminates any intermittent contact problems between the formed flat leads 38 and electrical conductors 42. In addition, the "self-aligning" relationship between formed flat leads 38 and electrical conductors 42 as they fit within their respective channels 46 greatly facilitates efficient electrical interconnection between chip carrier 34 and multiconductor lead 40, and eliminates any hand soldering of the electrical conductors.

Figure 9:
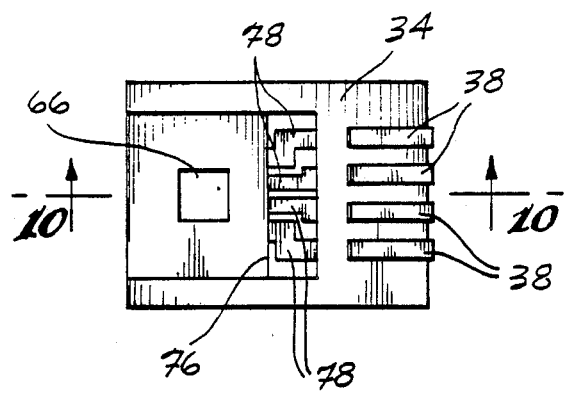
FIG. 9 is a plan view of a pressure transducer chip carrier.
Figure 10:
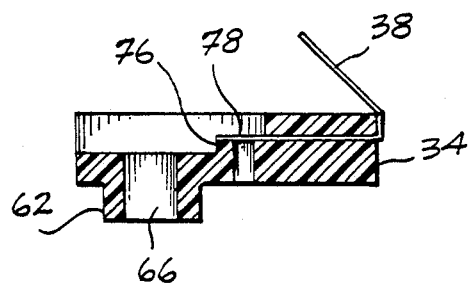
FIG. 10 is a cross-sectional view of the chip carrier taken along section lines 10—10 of FIG. 9.

On the lower surface of chip carrier 34 is formed a round projecting nib 62. This nib is sized to fit snugly within an orifice 68, that is formed within lower housing section 30. Orifice 68 provides access into flow-through passage 22. A passage 66 is defined through the center of nib 62, providing fluid communication between fluid in a catheter line (not shown) that is attached to connectors 24 and a pressure sensing diaphragm 106 of solid-state pressure transducer chip 36. However, the fluid within the catheter line is not allowed to directly contact the pressure transducer chip. Instead, passage 66 is filled with a silicon gel 64 (or other suitable incompressible gel), which serves to couple the pressure of fluid within flow-through passage 22 to the solid-state pressure transducer chip 36. Details of the lower housing section 30 are shown in FIGS. 4 through 6, and of the chip carrier, in FIGS. 9 and 10.

Chip carrier 34 is provided as a prefabricated subassembly, on which solid-state pressure transducer chip 36 is premounted, passage 66 through nib 62 is filled with gel 64, and flat leads 38 formed with the required "U-shape." The chip carrier subassembly is mounted in lower housing 30 by insertion of nib 62 into orifice 68. Adhesive is applied to a plurality of grooves 84 that are disposed in the upper interior surface of lower housing 30. The adhesive runs down grooves 84 and seals the interface between the exterior surface of nib 62 and the inner surface of orifice 68. Capillary attraction draws the adhesive from grooves 84 into voids between these surfaces. For this reason, a relatively thin adhesive is preferably used, such as a low viscosity polyurethane adhesive. The final step in the assembly process involves adhesively securing the upper housing section 32 to the lower housing section 30 using a cyanoacrylate adhesive applied to the outer surface of a lip 80 that is formed around the periphery of upper housing section 32. Lip 80 is then inserted within the peripheral extent of the lower housing and held in place until the adhesive sets.

It should be apparent that relatively little labor is required to assemble pressure transducer 20, due primarily to the use of the subassembly comprising chip carrier 34 in which the solid-state pressure transducer chip 36 is premounted, and also due to the ease with which the electrical connection between chip carrier 34 and electrical conductors 42 is effected, as described above. Consequently, the manufacturing (labor) cost of assembling blood pressure transducer 20 is relatively low compared to the prior art. In addition, unlike the pressure transducers used in the prior art, a solid-state pressure transducer is used in the present invention, which does not require a separate thick film hybrid circuit board on which discrete components are mounted. Instead, solid-state pressure transducer chip 36 includes a thin film compensation circuit that is fitted into the existing semiconductor environment on the chip.

Figure 12:
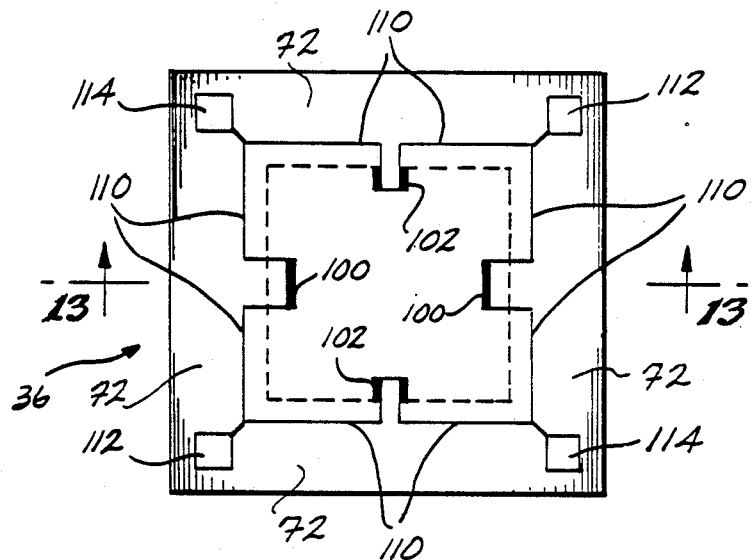
FIG. 12 is a schematic representation of a solid-state pressure transducer chip used in the present invention.
Figure 13:
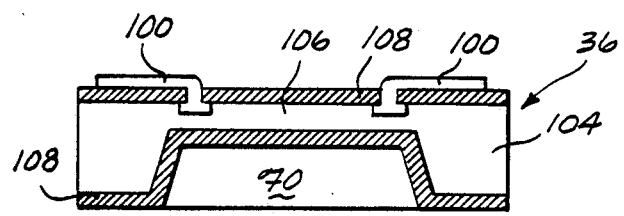
FIG. 13 shows the solid-state pressure transducer in a cross-sectional view taken along section lines 13—13 of FIG. 12.

Details of the pressure sensing circuit used on solid-state pressure transducer chip 36 are shown schematically in FIGS. 12 and 13. (The thin film compensation circuit is not shown in these Figures.) Solid-state pressure transducer chip 36 is generally conventional in its operation as a piezoresistive silicon pressure sensor, and includes P-type regions comprising sensing resistors 100 and 102, disposed in an N-type silicon wafer 104. The center of the N-type silicon wafer 104 comprises a relatively thin pressure sensing silicon diaphragm 106. Layers of silicon oxide 108 insulate the surface of silicon wafer 104.

The P-type regions comprising sensing resistors 100 and 102 are disposed in silicon wafer 104 adjacent the top surface of silicon diaphragm 106, around the edge of an underlying cavity 70, and are connected by conductors 110 in a standard Wheatstone bridge circuit. The thin film hybrid circuit used to compensate solid-state pressure transducer chip 36 for changes in temperature comprises a plurality of trimming resistors (not shown) incorporated on silicon wafer 104 in regions 72, disposed around the periphery of the chip, outside conductors 110.

Application of unequal fluid pressures on opposite surfaces of silicon diaphragm 106 causes it to deflect, the resulting strain changing the relative resistances of the sensing resistors 100 and 102. If the pressure transducer chip is exposed to the same pressure on opposite surfaces of the silicon diaphragm 106, the resistance of resistors 100 and 102 are substantially equal. Accordingly, under this balanced condition, if a voltage is applied to nodes 114 at diagonally opposite corners of the bridge, the potential difference between nodes 112 at the other two corners is approximately zero. However, if the center of silicon diaphragm 106 is deflected by unequal fluid pressures, applied to opposite surfaces, the potential difference between nodes 112 changes in direct proportion to the differential pressure, the resistance of sensing resistors 100 increasing, and the resistance of sensing resistors 102 decreasing by equal amounts, due to the unbalanced condition of the Wheatstone bridge. Pressure transducer 36 thus provides an output voltage between nodes 112 that is proportional to gage pressure when a pressure to be measured is applied to one surface of the center of silicon diaphragm 106, and ambient pressure is applied to the opposite surface.

Figure 11:
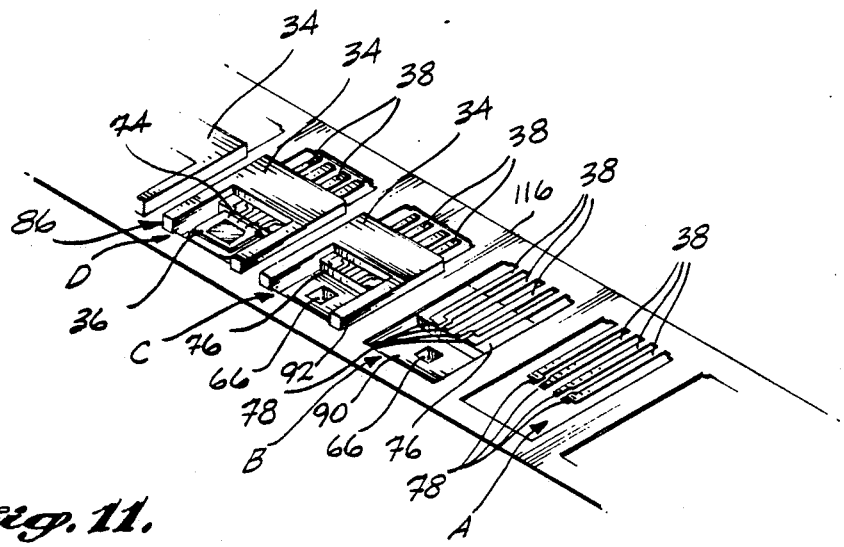
FIG. 11 is an isometric view showing sequential assembly of the chip carrier on a metal strip.

A further aspect of the present invention relates to the automated manufacture of the subassembly comprising chip carrier 34, shown sequentially in steps A through D in FIG. 11. Initially, a thin, flexible, metal strip 116 is run through a progressive die (not shown), forming a plurality of cut-out rectangular areas in which are defined the plurality of leads 38 (step "A"). Metal strip 116 is nickel-plated to provide a base coat for additional metal plating that is applied to leads 38. Specifically, the inwardly extending ends 78 of leads 38 are gold plated, providing a surface for attachment of gold "fly" wires 74, which are used to connect leads 38 to gold plated conductive pads (not shown) on the solid-state pressure transducer chip 36. The opposite ends of leads 38, still attached to metal strip 116, are tinned with a lead/tin solder or gold plated to provide a conductive path when in contact with electrical conductors 42 of lead 40.

In step "B," the lower and upper portions 90 and 92 of chip carrier 34 are integrally molded around metal strip 116 so that a shelf 76 formed thereon underlies the gold plated ends 78, and so that the edges of the lower portion are generally aligned with the edges of one of the die-cut openings within metal strip 116. Upper portion 92 is generally rectangular, having a relatively wide slot formed in one end. (For clarity, the upper portion 92 is shown cut away in the view of step 8.) The ends of leads 38 are then die-cut away from metal strip 116 in step "C." An opening is defined by the slot in the upper portion, exposing a surface within the lower portion on which the solid-state pressure transducer chip 36 is mounted, with cavity 70 overlying passage 66, (in step "D"). In addition, gold plated pads on the upper surface of the pressure transducer chip 36 are electrically connected to the gold plated ends 76 of flat leads 38 by means of gold fly wires 74. Once chip carrier 34 is fully assembled on metal strip 116 in a subassembly generally denoted by reference numeral 86, it is inverted and passage 66 on nib 62 is filled with silicon gel. It will be apparent that sub-assembly 86 may be fabricated in a substantially automated process. The metal strip with attached sub-assemblies 86 may be rolled-up on a reel (not shown) for later use in fabricating blood pressure transducer 20.

Prior to use in fabricating the blood pressure transducer 20, the metal strip 116 (on which are disposed the completed chip carrier subassemblies 86) is run through a punch which removes each chip carrier 34 from the strip and forms flat leads 38 into the required "U-shape" described above. The pre-assembly of chip carrier 34 and solid-state pressure transducer chip 36 into subassembly 86 thus greatly facilitates the ease of fabrication of the blood pressure transducer 20.

Figure 14:
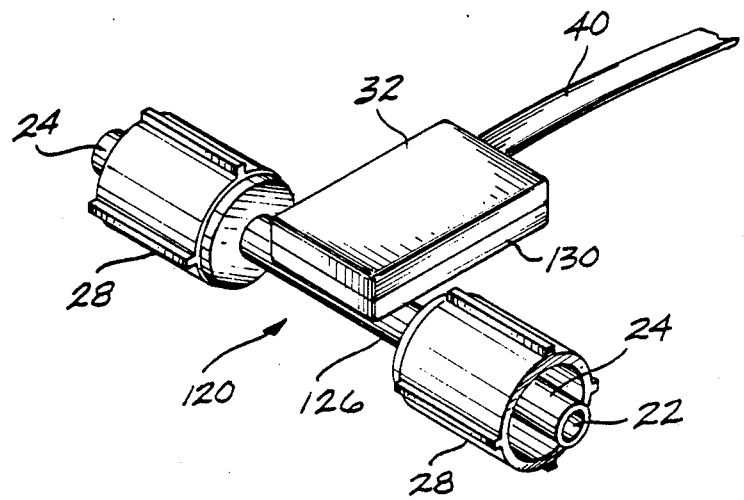
FIG. 14 is an isometric view showing a second embodiment of the blood pressure transducer; and, FIG. 15 is an electrical schematic diagram showing a resistor switching circuit provided in connectors used with the lead of the blood pressure transducer.

Turning now to FIG. 14, a second embodiment of the blood pressure transducer generally denoted by reference numeral 120 is shown. Blood pressure transducer 120 differs from the first embodiment 20 primarily with respect to the orientation of flow-through passage 22 and capillary line connectors 24. In the second embodiment, a lower housing section 130 includes an integral tubular portion 126 through which flow-through passage 22 extends. The tubular section 126 extends across the width of lower housing section 130, instead of longitudinally along its length, as was the case with respect to tubular section 26 on lower housing section 30 of the first embodiment. In all other respects, blood pressure transducers 20 and 120 are substantially the same. For this reason, the interior configuration of lower housing section 130 and upper housing section 32, and the mounting of chip carrier 34 therein are not shown. The same reference numerals are used on elements common to both embodiments.

Figure 15:
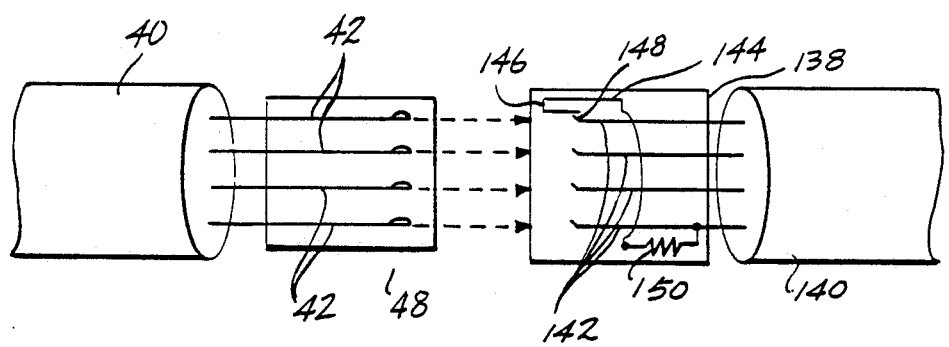

A further aspect of the present invention is shown in the schematic diagram of FIG. 15. Certain blood pressure monitoring devices have a relatively low input impedance requirement, and will not respond to a DC voltage from a high impedance source, such as solid-state pressure transducer chip 36. A cable 140 terminated in a modified female connector 138 is provided for such monitoring devices, as shown in FIG. 15. Female connector 138 includes a resistor 150, which is connected at one end to one of the conductors 142 within cable 140. The other end of resistor 150 is connected through lead 144 to a normally open switch contact 146. When modular connector 48 is plugged-in to female connector 138, the terminal end of the uppermost electrical conductor makes contact with its respective conductor 142, and forces the end 148 of that conductor to close against switch contact 146. Engagement of modular connector 48 and female connector 138 thus places resistor 150 in parallel with the outermost conductors in both lead 40 and cable 140. Since the outermost conductors of lead 40 carry the output signal from the solid-state pressure transducer chip 36, the monitoring device "sees" the required impedance on its input provided by the parallel resistance of resistor 150. Typically resistor 150 has a resistance of about 375 ohms, providing an output impedance to the monitoring device of about 300–350 ohms.

In prior art blood pressure transducers, an impedance matching resistor similar in function to resistor 150 is typically mounted in the transducer housing. There are at least three significant advantages which result from mounting resistor 150 in female connector 138 rather than in housing sections 30/130 and 32: (a) although blood pressure transducers 20 and 120 are disposable, cable 140 is not, being instead left connected to the monitoring device; thus, there is only a one-time cost for resistor 150 during the useable life of cable 140; (b) the housing sections 30/130 and 32 may be made smaller in size by mounting resistor 150 in female connector 138; and (c) most importantly, the heat dissipated by resistor 150 does not affect the thermal stability of solid-state pressure transducer chip 36 as it would if co-mounted inside the same housing. With respect to the third advantage (c), tests have shown that compared to prior art devices in which the impedance matching resistor is mounted inside the blood pressure transducer housing, the present invention exhibits less than 30% of the thermal drift during the initial warmup period, and stability is achieved in about one-third the time (80 seconds versus 240 seconds).

While the present invention has been disclosed with respect to preferred embodiments thereof, those of ordinary skill in the art will understand that further modifications to the invention may be made within the scope of the claims that follow hereinbelow. Accordingly, it is not intended that the scope of the invention be limited to what has been disclosed above but, instead, should be determined entirely by reference to the claims that follow.

The embodiments of the invention in which an exclusive property or priviledge is claimed are defined as follows:

1. Apparatus for measuring fluid pressure in a fluid line, comprising:
   (a) a pressure transducer comprising a semiconductor circuit on which are disposed a plurality of electrical contacts, and a pressure sensitive surface, said pressure sensitive surface experiencing a strain as a pressure is applied thereto, the strain causing the pressure transducer to produce an output signal, which varies as a function of the pressure, through the plurality of electrical contacts disposed on the semiconductor circuit;
   (b) a housing defining a cavity in which the pressure transducer is disposed and including a connector adapted to attach to the fluid line, the housing further including a fluid passage extending through the housing, proximate to the pressure sensitive surface of the pressure transducer and providing communication of fluid pressure between the connector and said pressure sensitive surface;
   (c) a plurality of insulated electrical conductors through which electrical signals are conveyed to and from the pressure transducer; and
   (d) an integrally formed chip carrier mounted in the cavity, said pressure transducer being attached to the chip carrier, said chip carrier including:
      (i) a fluid interface between the fluid passage and the pressure transducer, said interface including means for transmitting fluid pressure between the fluid passage and the pressure sensitive surface;
      (ii) a quick-connect electrical interface between the plurality of electrical conductors and the plurality of electrical contacts on the semiconductor circuit of the pressure transducer; and, (iii) means for sealing the pressure transducer within the cavity so that one side of the pressure sensitive surface is exposed to the means for transmitting fluid pressure and so that the opposite side thereof is isolated from the fluid passage and the fluid pressure therein.

2. The apparatus of claim 1, wherein the quick-connect electrical interface of the chip carrier includes a plurality of leads connected to the electrical contacts on the semiconductor circuit of the pressure transducer, and wherein the leads are formed in a "U" shape and engage the electrical conductors by spring force.

3. The apparatus of claim 2, wherein a bond area at an end of each lead is disposed on the carrier proximate the pressure transducer and is connected to the electrical contacts on the semiconductor circuit with fine wires.

4. The apparatus of claim 1, wherein the chip carrier comprises a generally planar surface, having a recess formed therein in which the pressure transducer is mounted, and an aperture formed in the recess over which the pressure sensitive surface of the pressure transducer is disposed.

5. The apparatus of claim 4, wherein the recess includes a shelf on which is disposed a plurality of lead bond areas, said bond areas being connected to a plurality of leads that extend from the chip carrier and outwardly of an end thereof.

6. The apparatus of claim 4, wherein a nib projects from a surface of the chip carrier opposite that in which the recess is formed, said nib being disposed around the aperture and extending into engagement with a receptacle formed in the housing, in fluid communication with the fluid passage.

7. The apparatus of claim 6, wherein said means for transmitting fluid pressure comprises a substantially incompressible gel, and wherein the nib is filled with the gel.

8. The apparatus of claim 1, wherein the housing comprises a first section on which the electrical conductors are terminated and a second section on which the connector is disposed, said first and second sections being sealingly joined after the chip carrier and pressure transducer are mounted in the cavity.

9. The apparatus of claim 1, wherein the pressure transducer comprises a piezoresistive type transducer, including a plurality of resistors connected in a Wheatstone bridge configuration.

10. The apparatus of claim 9, wherein the semiconductor circuit further comprises means for temperature compensating the resistance of the resistors.

11. The apparatus of claim 1, wherein the insulated electrical conductors include a resistor, which is connected in parallel with the output signal from the pressure transducer to reduce the apparent impedance of the pressure transducer relative to a device connected to monitor its output signal.

12. In a catheter system, a pressure sensing apparatus adapted to attach to a catheter and operative to produce an electrical signal indicative of the magnitude of fluid pressure in the catheter, said apparatus comprising:
(a) pressure sensing means, including a first and a second surface, for sensing a differential fluid pressure applied between the first surface and the second surface thereof and producing an electrical signal indicative of the magnitude of the fluid pressure, said second surface thereof including contact means for connecting the electrical signal to a plurality of discrete conductors;
(b) housing means for enclosing the pressure sensing means, including:
(i) connector means for providing a sealed connection to a line in fluid communication with the catheter system,
(ii) passage means for conveying a fluid from the connector means to a point within the housing means proximate the first surface of the pressure sensing means, and
(iii) an electrical cable for conveying the electrical signal from the pressure sensing apparatus; and
(c) carrier means, disposed within the housing means, for:
(i) integrally defining a sealed aperture disposed between the first surface of the pressure sensing means and the passage means, including pressure transmitting means disposed in the aperture for transmitting fluid pressure from the fluid in the passage means to the first surface of the pressure sensing means,
(ii) mounting the pressure sensing means within the housing means in sealed relationship with the fluid passage means, and
(iii) conducting the electrical signal from the plurality of discrete conductors to the electrical cable through a plurality of spring biased leads, which are disposed on the carrier means.

13. The apparatus of claim 12, wherein the electrical cable comprises a plurality of insulated wires, each wire being stripped of insulation at an end portion that is terminated in the housing means, said leads in the carrier means being formed in a "U" shaped loop that is spring biased to engage the end portions of the wires, forming a conductive contact therewith.

14. The apparatus of claim 12, wherein the housing means comprise a first and a second section, opposed mating surfaces of the first and the second section defining therebetween a cavity in which the carrier means and pressure sensing means are disposed.

15. The apparatus of claim 14, wherein the first section of the housing means is attached to the electrical cable and the second section is attached to the connector means.

16. The apparatus of claim 14, wherein the pressure sensing means are mounted on the carrier means and the plurality of discrete conductors are attached between the spring biased leads and the contact means forming an assembly, and wherein said assembly is sealed into the cavity by mating the first section of the housing means to the second section.

17. The apparatus of claim 14, wherein the carrier means include a nib disposed around said aperture proximate the first surface of the pressure sensing means and projecting into the passage means, said pressure transmitting means being disposed within said nib.

18. The apparatus of claim 17, wherein the pressure transmitting means comprise a substantially incompressible gel, which seals the aperture, preventing fluid communication between the passage means and the first surface of the pressure sensing means.

19. The apparatus of claim 17, wherein the housing means include an adhesive channel, said first and second sections of the housing means being joined with an adhesive, said adhesive flowing through the adhesive channel to join and the seal the nib to the housing means.

20. The apparatus of claim 12, wherein the pressure sensing means comprise a thin film semiconductor circuit disposed on the periphery of the second surface and a pressure sensitive diaphragm disposed on the center of the first and the second surfaces.

21. A method for assembling a pressure sensing device useful for measuring pressure in a catheter system, said pressure sensing device including a pressure transducer having a pressure sensing surface and a plurality of electrical contacts, a chip carrier, an electrical cable including a plurality of conductors, and a housing, comprising the steps of:

(a) attaching the pressure transducer to the chip carrier;

(b) bonding wires to the electrical contacts and to a plurality of lead areas disposed on the chip carrier, providing an electrically conductive path therebetween;

(c) forming a plurality of leads that are attached to the chip carrier, generally into a "U" shape;

(d) filling an aperture disposed on the clip carrier adjacent the pressure sensing surface of the pressure transducer with a substantially incompressible gel;

(e) mounting the chip carrier with the pressure transducer attached in a recess formed in a first portion of the housing, with the aperture in fluid communication with a catheter connector formed on the housing, said catheter connector adapting the housing for connection to the catheter system;

(f) positioning the cable in an opening formed within the housing so that the formed leads engage the plurality of conductors in the electrical cable; and (g) securing a second portion of the housing to the first portion, so that the pressure transducer and chip carrier are sealed within the housing.

22. The method of claim 21, wherein the aperture is defined by a projecting nib disposed on the chip carrier, the step of mounting the chip carrier in a first portion of the housing including the step of seating the projecting nib into a mating receptacle formed on the interior of the first portion of the housing.

23. The method of claim 22, wherein the projecting nib is filled with the incompressible gel.

24. The method of claim 21, wherein the second portion of the housing is secured to the first portion thereof with an adhesive.

25. Apparatus for mounting a pressure transducer comprising:

(a) a baseplate having a recessed portion on which a generally planar surface is formed, said recessed portion including an aperture that extends through the baseplate;

(b) a plurality of electrically conductive leads that extend outwardly from an end of the baseplate, into the recessed portion; and (c) a lead bond area disposed within the recessed portion, on which is terminated an end of each of the leads that are adapted to be electrically connected to the pressure transducer.

26. The apparatus of claim 25, wherein the baseplate is adapted to mount the pressure transducer in an automated process by its attachment to a thin flexible strip in which a plurality of similar baseplates are attached and carried.

27. The apparatus of claim 26, wherein the baseplate is attached to the thin flexible strip during its manufacture.

28. The apparatus of claim 26, wherein the plurality of electrically conductive leads are formed from the thin, flexible strip during manufacture of the apparatus.

29. The apparatus of claim 25, wherein the aperture extends through a nib that projects outwardly of the baseplate, and which is adapted to be filled with a substantially incompressible gel.

30. The apparatus of claim 25, wherein the lead bond area is disposed on a shelf formed in the recessed portion of the baseplate, and the leads extend through the baseplate, the ends of the leads being plated with a precious metal of relatively higher electrical conductivity than a metal from which the leads are formed.

31. The apparatus of claim 25, wherein the baseplate is generally rectangular in shape and comprises a top portion and a bottom portion disposed on opposite surfaces of the thin flexible strip.

* * * * *